United States Patent
Wakai et al.

(10) Patent No.: US 10,405,817 B2
(45) Date of Patent: Sep. 10, 2019

(54) X-RAY IMAGE DIAGNOSIS APPARATUS AND MEDICAL SYSTEM

(71) Applicant: Toshiba Medical Systems Corporation, Otawara-shi (JP)

(72) Inventors: Satoshi Wakai, Nasushiobara (JP); Tetsuya Yokota, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 866 days.

(21) Appl. No.: 14/996,470

(22) Filed: Jan. 15, 2016

(65) Prior Publication Data

US 2016/0206260 A1    Jul. 21, 2016

(30) Foreign Application Priority Data

Jan. 16, 2015 (JP) .................. 2015-007200

(51) Int. Cl.
*A61B 8/00*    (2006.01)
*A61B 6/00*    (2006.01)
(Continued)

(52) U.S. Cl.
CPC ............ *A61B 6/4417* (2013.01); *A61B 6/032* (2013.01); *A61B 6/463* (2013.01); *A61B 6/503* (2013.01); *A61B 6/54* (2013.01); *A61B 8/06* (2013.01); *A61B 8/12* (2013.01); *A61B 5/055* (2013.01); *A61B 6/504* (2013.01)

(58) Field of Classification Search
CPC ...................................................... A61B 8/00
See application file for complete search history.

(56) References Cited

U.S. PATENT DOCUMENTS

2011/0130668 A1* 6/2011 Ohyu .................. A61B 5/0263
                                                      600/504
2012/0106815 A1    5/2012 Yang et al.
(Continued)

FOREIGN PATENT DOCUMENTS

JP    2011-131041 A    7/2011
JP    2012-90978 A     5/2012
(Continued)

OTHER PUBLICATIONS

Office Action dated Aug. 28, 2018 in Japanese Patent Application No. 2015-007200.

*Primary Examiner* — Omkar A Deodhar
(74) *Attorney, Agent, or Firm* — Oblon, McClelland, Maier & Neustadt, L.L.P.

(57) ABSTRACT

An X-ray image diagnosis apparatus includes an X-ray tube, an X-ray detector, a fluid information acquisition unit, a registration unit, and a capturing direction controller. The X-ray tube emits X-rays toward a subject. The X-ray detector detects the X-rays having passed through the subject. The fluid information acquisition unit acquires fluid information on a target site including a region of interest of the subject captured by an ultrasound image diagnosis apparatus. The registration unit extracts position information of a probe of the ultrasound image diagnosis apparatus. The capturing direction controller controls capturing direction for capturing the target site based on the position information and a direction in which a fluid flows indicated by the fluid information.

10 Claims, 15 Drawing Sheets

(51) Int. Cl.
*A61B 6/03* (2006.01)
*A61B 8/06* (2006.01)
*A61B 8/12* (2006.01)
*A61B 5/055* (2006.01)

(56) References Cited

U.S. PATENT DOCUMENTS

2012/0245458 A1* 9/2012 Gogin .................. A61B 6/00
                                                    600/424
2015/0093010 A1   4/2015 Yang et al.

FOREIGN PATENT DOCUMENTS

| JP | 2013-513412 | 4/2013 |
| JP | 2014-79441 A | 5/2014 |
| JP | 2014-200549 A | 10/2014 |

* cited by examiner

X-RAY IMAGE DIAGNOSIS APPARATUS AND MEDICAL SYSTEM

CROSS-REFERENCE TO RELATED APPLICATION

This application is based upon and claims the benefit of priority from Japanese Patent Application No. 2015-007200, filed Jan. 16, 2015; the entire contents of which are incorporated herein by reference.

FIELD

Embodiments described herein relate generally to an X-ray image diagnosis apparatus and a medical system.

BACKGROUND

In recent years, trans-catheter aortic valve replacement (TAVR) has become increasingly used for the treatment of aortic stenosis. In TRVR, a surgical valve (prosthetic valve) is delivered via a catheter to the heart. During TAVR, transesophageal ultrasound (3D Transesophageal Echo: 3D-TEE) imaging is often performed to evaluate the reverse blood flow in a region of interest (a space between the aorta and the prosthetic valve) while the region is being observed by using an angiography apparatus, i.e., one example of the X-ray image diagnosis apparatus. In the transesophageal ultrasound (3D-TEE) imaging, a probe is inserted through the nose or the mouth to perform echocardiography in a subject's body (esophagus).

There has been proposed a technology, in which a transesophageal ultrasound (3D-TEE) image is read and displayed in fusion with an angiography image in real time.

Note that the trans-catheter aortic valve replacement may be sometimes called "trans-catheter aortic valve implantation (TAVI)". Examples of the prosthetic valve include mechanical valves made of carbon resin or the like and bioprosthetic valves obtained by processing biological material such as animal tissue.

DETAILED DESCRIPTION

Figure 1:
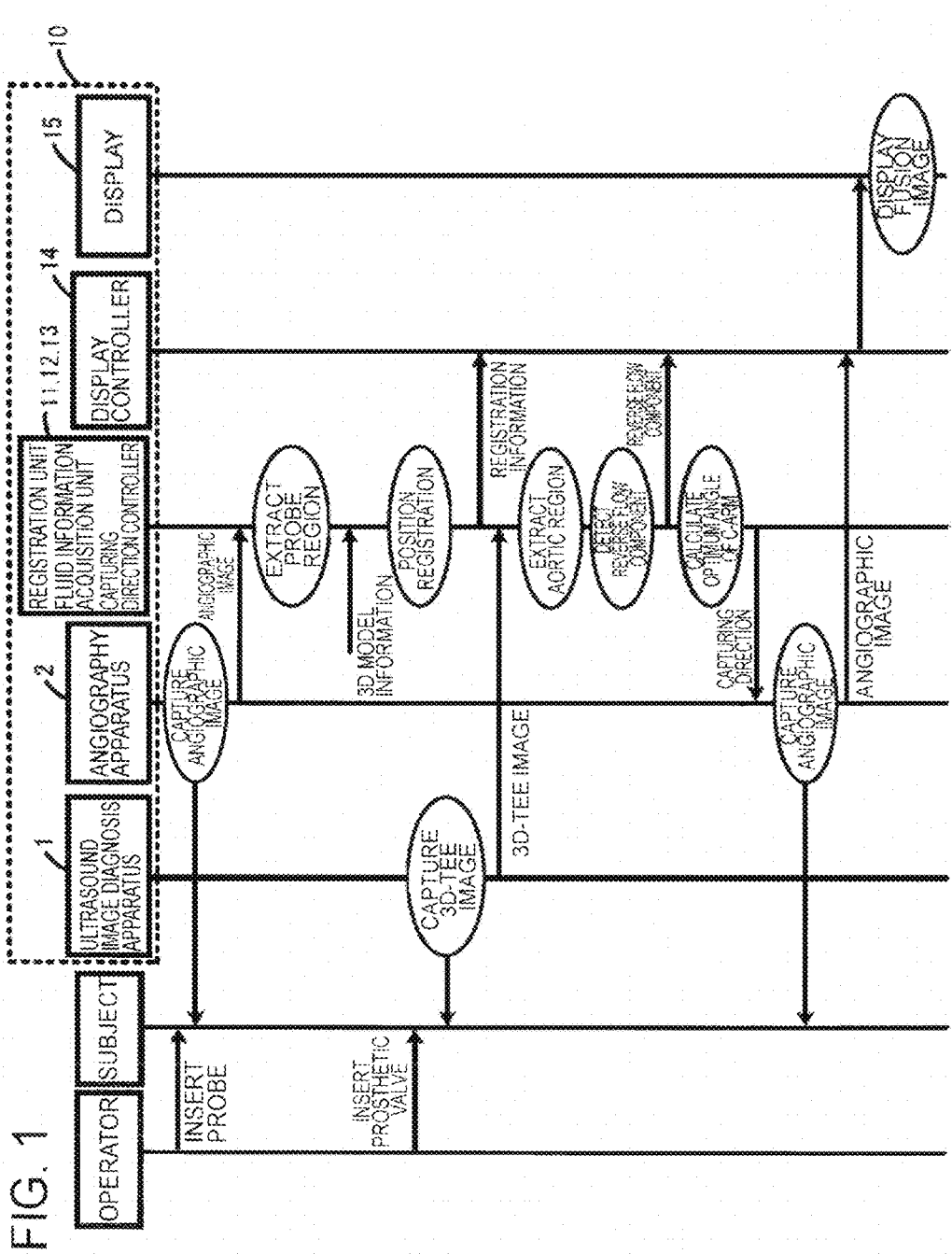
FIG. 1 is a timing chart illustrating the operation of a medical system according to a first embodiment.

In general, according to one embodiment, an X-ray image diagnosis apparatus includes an X-ray tube, an X-ray detector, a fluid information acquisition unit, a registration unit, and a capturing direction controller. The X-ray tube emits X-rays toward a subject. The X-ray detector detects the X-rays having passed through the subject. The fluid information acquisition unit acquires fluid information on a target site including a region of interest of the subject captured by an ultrasound image diagnosis apparatus. The registration unit extracts position information of a probe of the ultrasound image diagnosis apparatus. The capturing direction controller controls capturing direction for capturing the target site based on the position information and a direction in which a fluid flows indicated by the fluid information.

According to another embodiment, a medical system includes an X-ray image diagnosis apparatus including an X-ray tube that emits X-rays toward a subject, and an X-ray detector that detects the X-rays having passed through the subject, and an ultrasound image diagnosis apparatus configured to capture a target site including a region of interest of the subject. The X-ray image diagnosis apparatus further includes a fluid information acquisition unit, a registration unit, and a capturing direction controller. The fluid information acquisition unit acquires fluid information on the target site. The registration unit extracts position information of a probe of the ultrasound image diagnosis apparatus. The capturing direction controller controls capturing direction for capturing the target site based on the position information and a direction in which a fluid flows indicated by the fluid information.

Described below is an overview of one embodiment.

This embodiment is intended to control the capturing direction when an image is captured by a second medical image diagnosis apparatus based on fluid information (e.g., blood flow information) obtained from an image captured by a first medical image diagnosis apparatus. Accordingly, the configuration varies depending on the type of the first medical image diagnosis apparatus and the second medical image diagnosis apparatus, the site to be captured (target site), and the definition of the fluid information (blood flow information).

In addition, there is provided a registration unit configured to perform registration between an image captured by the first medical image diagnosis apparatus and an image captured by the second medical image diagnosis apparatus to display a combined image of them.

In the first embodiment, the first medical image diagnosis apparatus is an ultrasound image diagnosis apparatus 1 capable of transesophageal ultrasound imaging. The second medical image diagnosis is an angiography apparatus 2 as an example of the X-ray image diagnosis apparatus. The target site includes a region of interest as a space between the aorta and a prosthetic valve inserted thereto. The blood flow information includes information on a forward flow component as a normal blood flow and a reverse flow component as an abnormal blood flow in the region of interest. In the first embodiment, the reverse flow component represents an abnormal blood flow in the aortic region, and is determined based on the threshold (described later) of the image signal value. Note that the term "reverse flow component" represents the concept that includes the magnitude and direction of the blood flow (and/or an axis representing the reverse flow component such as, for example, a reverse flow component axis described later).

FIG. 1 is a timing chart illustrating the operation of a medical system according to the first embodiment. In the first embodiment, trans-catheter aortic valve replacement (TAVR) is performed following the procedure as illustrated in FIG. 1:

(1) An operator inserts a probe through the mouth or the nose into the esophagus of a subject, and captures an image of the probe in the subject by using the angiography apparatus 2.

(2) A registration unit 11 extracts a probe region (position information) from the angiographic image captured, compares it with three-dimensional (3D) model information, and determines the position and orientation of the probe adjusted to be directed to the region of interest based on the comparison result. The position and orientation of the probe thus determined serves as registration information for position registration between an image captured by the ultrasound image diagnosis apparatus 1 and an image captured by the angiography apparatus 2.

(3) After the position and orientation of the probe is adjusted, transesophageal ultrasound imaging is performed by the probe directed to the region of interest to capture a transesophageal ultrasound image.

(4) A fluid information acquisition unit 12 extracts an aortic region from the transesophageal ultrasound image to detect a reverse flow component.

(5) A capturing direction controller 13 calculates the optimum angle of the C-arm based the reverse flow component, and controls the capturing direction of the angiography apparatus 2 to have less overlap between the reverse flow component and the prosthetic valve as viewed from the capturing direction. The angiography apparatus 2 captures the subject, and acquires an angiographic image.

(6) A display controller 14 displays, on a display 15, a fusion image formed of a combination of the angiographic image and the transesophageal ultrasound image in real time with reference to the registration information.

(7) The operator refers to the fusion image to evaluate the reverse flow component.

In the second embodiment, the capturing direction controller 13 is configured to control the capturing direction to have less overlap between tricuspid aortic valves and/or the origins of the coronary arteries as target sites in addition to between the reverse flow component and the prosthetic valve as viewed from the capturing direction.

In the third and fourth embodiments, the fluid information acquisition unit 12 detects a reverse flow component in the region of interest not from a transesophageal ultrasound image, but from a computed tomography (CT) image or a magnetic resonance imaging (MRI) image captured by an X-ray CT apparatus or an MRI apparatus.

First Embodiment

Figure 2:
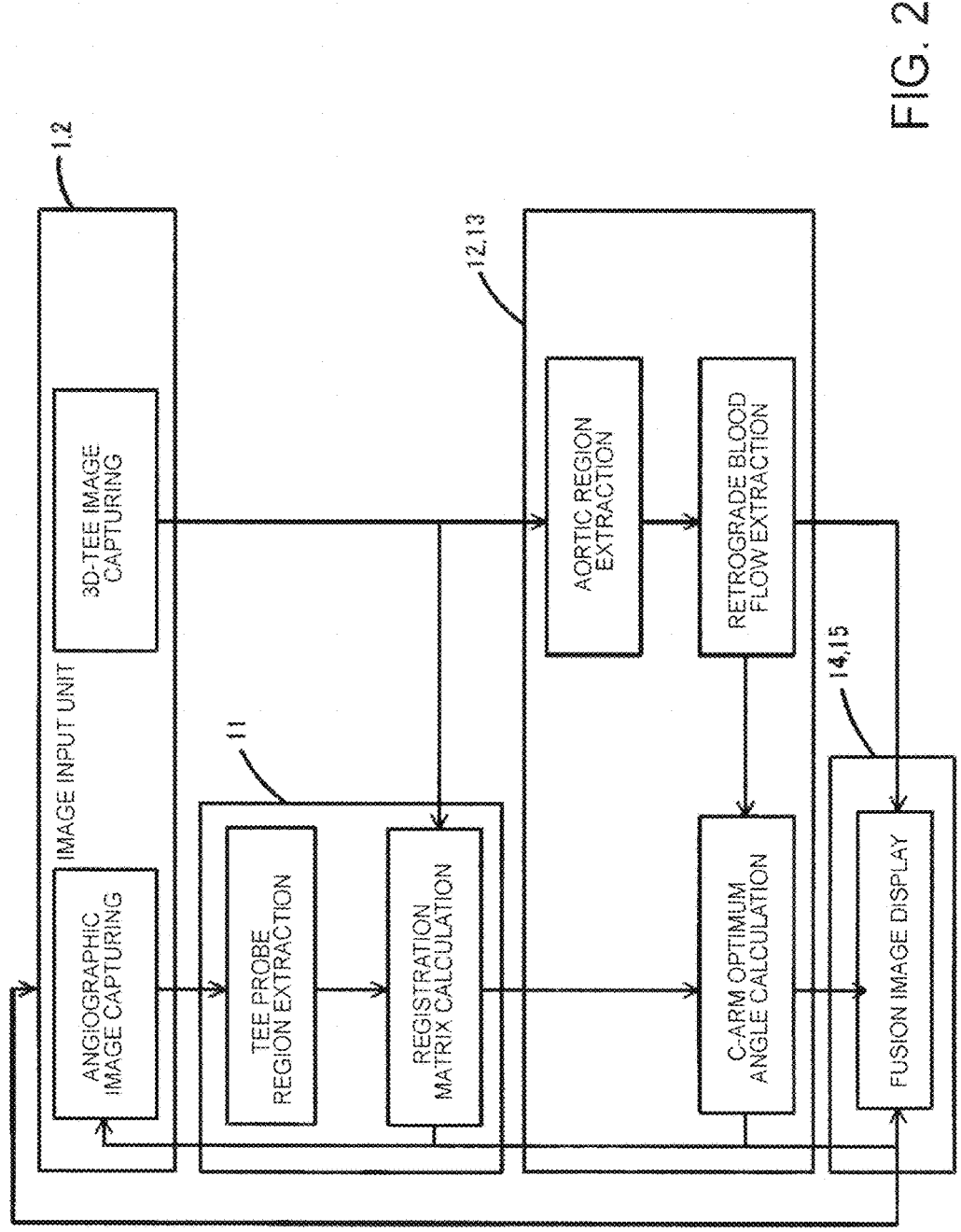
FIG. 2 is a block diagram of the medical system of the first embodiment.

With reference to FIGS. 1 to 5, a description is given of a medical system 10 according to the first embodiment. FIG. 2 is a block diagram of the medical system 10. The medical system 10 includes the registration unit 11, the fluid information acquisition unit 12, the capturing direction controller 13, the display controller 14, and the display 15. Having informed of a capturing direction by the capturing direction controller 13, the angiography apparatus 2 captures a region of interest to acquire an angiographic image. With reference to the registration information, the medical system 10 forms a fusion image of a combination of the angiographic image and a transesophageal ultrasound image, and displays it on the display 15 in real time.

Figure 6:
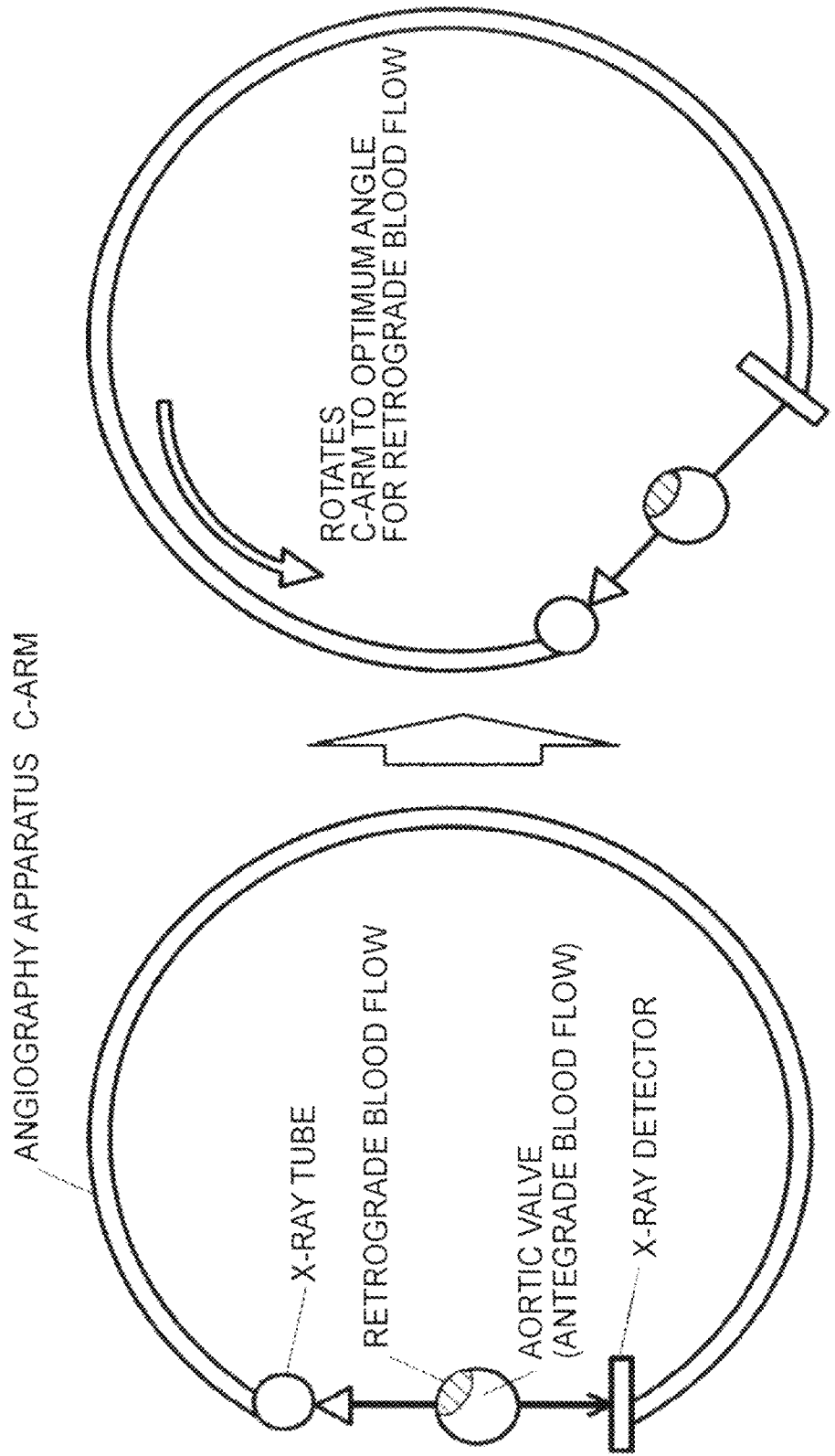
FIG. 6 is views of a C arm before and after the capturing direction is controlled.

The configuration of the angiography apparatus 2 is briefly described below. The angiography apparatus 2 includes a substantially C-shaped arm (hereinafter referred to as "C-arm"), a support mechanism (not illustrated) configured to rotatably support the C-arm, a rotation driver (not illustrated) configured to drive the rotation of the C-arm, an X-ray tube (not illustrated) mounted on the C-arm, an X-ray detector (not illustrated) mounted on the C-arm in a direction to face the X-ray tube, and a rotation controller (not illustrated) configured to control the rotation driver. FIG. 6 illustrates the C-arm, and the X-ray tube and the X-ray detector mounted thereon.

In TAVR, as illustrated in FIG. 1, the operator inserts a probe through the mouth or the nose into the esophagus of a subject, and the angiography apparatus 2 captures the probe in the subject ("angiographic image capturing" in FIG. 2). Next, the operator inserts a prosthetic valve into the aorta, and the ultrasound image diagnosis apparatus 1 captures a transesophageal ultrasound (3D-TEE) image ("3D-TEE image capturing" in FIG. 2,). It is assumed herein that the pixels of the angiographic image are arranged on the XYZ coordinates, and that the pixels of the transesophageal ultrasound (3D-TEE) image are drawn on the xyz coordinates.

(Registration Unit 11)

In TAVR, upon performing transesophageal ultrasound (3D-TEE) imaging, it is determined whether the probe is directed to the region of interest on the angiographic image. Further, at the final stage of TAVR, the reverse flow is evaluated with reference to a fusion image formed of a combination of an angiographic image captured by the angiography apparatus 2 and a transesophageal ultrasound (3D-TEE) image. The registration unit 11 is provided to register the angiographic image and the transesophageal ultrasound (3D-TEE) image to each other. In response to an instruction input through an operation unit (not illustrated), the registration unit 11 retrieves the angiographic image from the angiography apparatus 2, and extracts the contour of the probe (position information) from the angiographic image ("TEE probe region extraction" in FIG. 2). The registration unit 11 further retrieves a 3D model representing the shape of the probe from the outside, and compares the contour of the probe with the 3D model using a pattern matching technique. Thus, it is obtained that the center position of the transducer surface of the probe for transmitting and receiving ultrasound waves (hereinafter referred to as "position of the probe") is located at (a, b, c) on the XYZ coordinates, and the orientation of the transducer surface of the probe (hereinafter referred to as "orientation of the probe") is an orientation when the probe is rotated about the X axis, the Y axis, and the Z axis by $\alpha$, $\beta$, and $\gamma$, respectively. In the angiographic image captured by the angiography apparatus 2 from a predetermined capturing direction toward the region of interest, the position and orientation of the probe, which is directed to the region of interest, is determined in advance. At this time, the position of the probe is represented by a1, b1, and c1, and the orientation is represented by $\alpha 1$, $\beta 1$, and $\gamma 1$.

In other words, the operator adjusts the position and orientation of the probe until the position and the orientation correspond to a1, b1, c1, and $\alpha 1$, $\beta 1$, $\gamma 1$, respectively. Having determined that the position a, b, c and the orientation $\alpha$, $\beta$, $\gamma$ of the probe obtained by comparison match the position a1, b1, c1, and the orientation α1, β1, γ1, and the probe is directed to the region of interest, the registration unit 11 determines (settles) the position a, b, c and the orientation α, β, γ of the probe as registration information ("registration matrix calculation" in FIG. 2). The registration information obtained this time serves as a reference for registration between the angiographic image and the transesophageal ultrasound image. The registration unit 11 sends the registration information thus obtained to the display controller 14. A description is given later of the operation of the display controller 14 to display a combination of the angiographic image and the transesophageal ultrasound image with reference to the registration information. Regarding the pattern matching technique, reference may be had to, for example, JP-A No. 2009-160221 which discloses a technology, in which a 3D model of the heart is stored in the memory in advance to compare three-dimensional data obtained by capturing the heart with it, and the 3D model is fitted to the three-dimensional data as being deformed (position, angle, size).

(Fluid Information Acquisition Unit 12)

Before or after the acquisition of the registration information by the registration unit 11, a prosthetic valve is inserted into the aorta. In addition, after the registration unit 11 has acquired the registration information, the ultrasound image diagnosis apparatus 1 captures the region of interest to capture a transesophageal ultrasound (3D-TEE) image.

The fluid information acquisition unit 12 retrieves the transesophageal ultrasound image, which corresponds to volume data acquired in time series, from the ultrasound image diagnosis apparatus 1. The fluid information acquisition unit 12 extracts the aortic region, and generates a Doppler image that represents changes in the frequency of ultrasound beams (image signal value) at a particular position for each pixel. The fluid information acquisition unit 12 extracts a reverse flow component from the Doppler image with reference to the threshold of the image signal value for each pixel ("retrograde blood flow extraction" in FIG. 2). Further, the fluid information acquisition unit 12 specifies an image of a time phase, in which the reverse flow component has the largest volume, as most reverse flow time phase image. The fluid information acquisition unit 12 calculates a diffusion coefficient D in the three-dimensional space of reverse flow volume data in the most reverse flow time phase image to thereby obtain the direction of the reverse flow component, and defines it as a reverse flow component axis. Note that, for example, the blood is pumped to the aorta through the prosthetic valve from the left ventricle in the systolic phase of the cardiac cycle, and a reverse flow often occurs in the region of interest in the systole phase. Therefore, the transesophageal ultrasound image used for extracting the reverse flow component may be limited to a transesophageal ultrasound image in a predetermined time phase. In this case, the ultrasound image diagnosis apparatus 1 acquires the transesophageal ultrasound image in association with electrocardiograph (ECG) signal waveform data. The fluid information acquisition unit 12 selects a transesophageal ultrasound image in the systolic phase with reference to the ECG signal waveform data, and extracts a reverse flow component from the transesophageal ultrasound image. In addition, the diffusion coefficient D may be calculated for images of a plurality of time phases (e.g., images of time phases during systole) to obtain the directions of the reverse flow component, and one of them may be selected as the reverse flow component axis.

The diffusion coefficient D is obtained from the voxel value of volume data (or the pixel value of a reconstructed image or the signal value of raw data) with reference to the following equation (1) using, for example, the technique disclosed in JP-A No. 2012-90978:

[Equation 1]

$$\frac{\partial u}{\partial t} = \nabla \cdot (D(u)\nabla u) \quad (1)$$

where, u is a function that depends on three-dimensional coordinates and time (x, y, z, t) in the reverse flow volume data, and "·" represents the inner product of two vectors (∇ and D(u)∇u).

The fluid information acquisition unit 12 sends information on the reverse flow component to the display controller 14. A description is given later of the operation of the display controller 14 to display a combination of the angiographic image and the reverse flow component (transesophageal ultrasound image) with reference to the registration information.

The fluid information acquisition unit 12 also sends the reverse flow component axis defined to the capturing direction controller 13.

(Capturing Direction Controller 13)

The capturing direction controller 13 controls, based on the reverse flow component axis, the capturing direction θ (the optimum angle of the C-arm) to be a direction perpendicular to the reverse flow component axis as viewed from the capturing direction by the angiography apparatus 2, in which the reverse flow component can be observed from the side, with less overlap between the reverse flow component and a therapeutic valve ("C-arm optimum angle calculation" in FIG. 2,).

Figure 3:
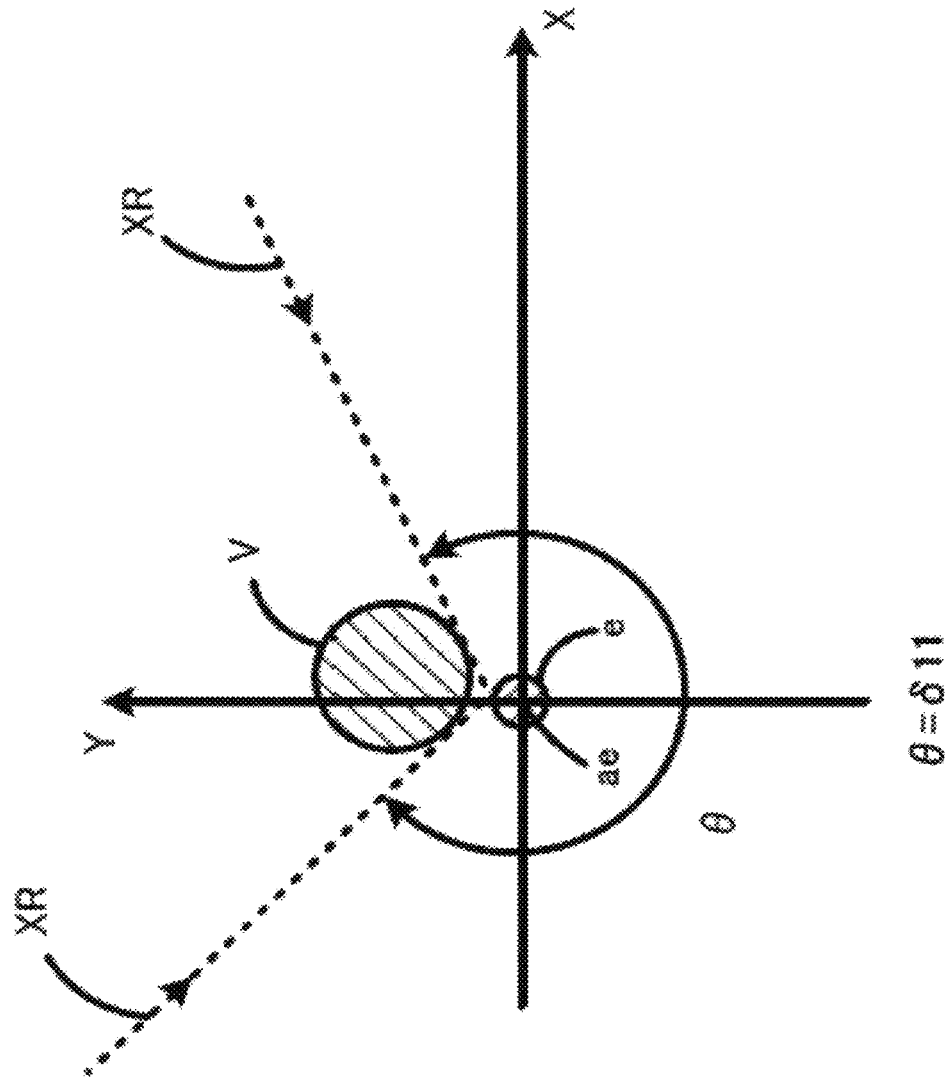
FIG. 3 is a diagram for calculating an capturing direction.
Figure 4:
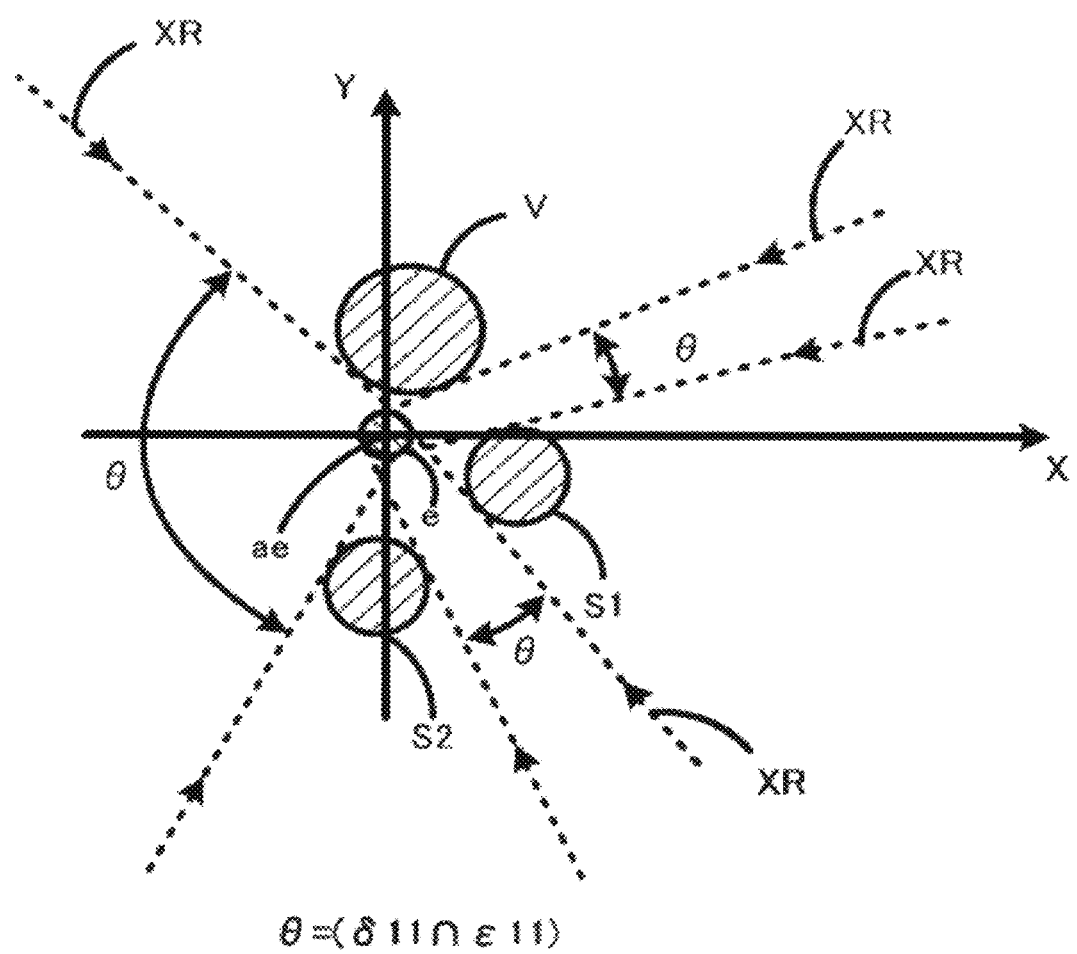
FIG. 4 is a diagram for calculating an capturing direction.

In the following, a description is given of how to obtain the capturing direction θ with reference to FIGS. 3 and 4. FIGS. 3 and 4 are explanatory views for explaining the calculation of the capturing direction.

(1) As illustrated in FIG. 3, for example, the reverse flow component axis ae is matched with any one of the X axis, the Y axis, and the Z axis (here, the Z axis). The coordinates of the reverse flow component axis ae are at X=0 and Y=0.

(2) When cross sections (hatched) are prepared along the XY plane with respect to the reverse flow component e and the therapeutic valve V, a capturing direction δi is obtained which satisfies the conditions that X-rays XR emitted from the X-ray tube toward the reverse flow component e along the XY plane are not to be irradiated to the cross section of the therapeutic valve V. In other words, the capturing direction δi is obtained such that X-rays XR irradiate the reverse flow component e while avoiding the therapeutic valve V.

(3) In this way, the capturing direction δi that satisfies the conditions is obtained from one end to the other end (Zi=Z1, Z2, . . . , Zn) in the longitudinal direction (Z axis) of the reverse flow component e to obtain (δi=δ1, δ2, . . . , δn). A capturing direction δ11 common to all between the one end and the other end is finally obtained as the capturing direction θ (see FIG. 3).

(4) As illustrated in FIG. 4, in addition to the therapeutic valve V, when there is/are one or more regions to be prevented from being irradiated with X-rays (e.g., the valve structure of the tricuspid aortic valves, the origins of the coronary arteries, or the like, described later), the same method as in the therapeutic valve V is applied to the cross section of each of regions S1 and S2 along the XY plane.

Specifically, a capturing direction εi that satisfies the conditions is obtained from one end to the other end of another region to obtain (εi=ε1, ε2, ... εn). A capturing direction ε11 common to all between the one end and the other end is finally obtained.

(5) The common direction between the capturing direction δ11 finally obtained for the therapeutic valve and the capturing direction ε11 finally obtained for another region is determined as the capturing direction θ finally obtained (see FIG. 4).

Incidentally, "to control the capturing direction to have less overlap" means to control the capturing direction to prevent X-ray exposure (radiation), or even if an exposure occurs, to reduce the exposure as much as possible.

The capturing direction controller 13 sends the capturing direction to the angiography apparatus 2. Having received the capturing direction, the rotation controller (not illustrated) of the angiography apparatus 2 controls the rotation driver (not illustrated). The angiography apparatus 2 captures the target site including the region of interest to capture an angiographic image. The angiography apparatus 2 sends the angiographic image to the display controller 14.

(Display Controller 14)

As described above, the display controller 14 receives the registration information from the registration unit 11, the reverse flow component (transesophageal ultrasound image) from the fluid information acquisition unit 12, and further, the angiographic image from the angiography apparatus 2. Using the registration information (the position a, b, c and the orientation α, β, γ of the probe), the display controller 14 converts the position of the pixel of the reverse flow component (transesophageal ultrasound image) drawn on the xyz coordinates to the XYZ coordinates with reference to the following equation (2):

[Equation 2]

$$\begin{bmatrix} X \\ Y \\ Z \\ 1 \end{bmatrix} = \begin{bmatrix} 1 & 0 & 0 & 0 \\ 0 & \cos\alpha & -\sin\alpha & 0 \\ 0 & \sin\alpha & \cos\alpha & 0 \\ 0 & 0 & 0 & 1 \end{bmatrix} \quad (2)$$

$$\begin{bmatrix} \cos\beta & 0 & \sin\beta & 0 \\ 0 & 1 & 0 & 0 \\ -\sin\beta & 0 & \cos\beta & 0 \\ 0 & 0 & 0 & 1 \end{bmatrix} \times \begin{bmatrix} \cos\gamma & -\sin\gamma & 0 & 0 \\ \sin\gamma & \cos\gamma & 0 & 0 \\ 0 & 0 & 1 & 0 \\ 0 & 0 & 0 & 1 \end{bmatrix} \begin{bmatrix} 1 & 0 & 0 & a \\ 0 & 1 & 0 & b \\ 0 & 0 & 1 & c \\ 0 & 0 & 0 & 1 \end{bmatrix} \begin{bmatrix} x \\ y \\ z \\ 1 \end{bmatrix}$$

Figure 5:
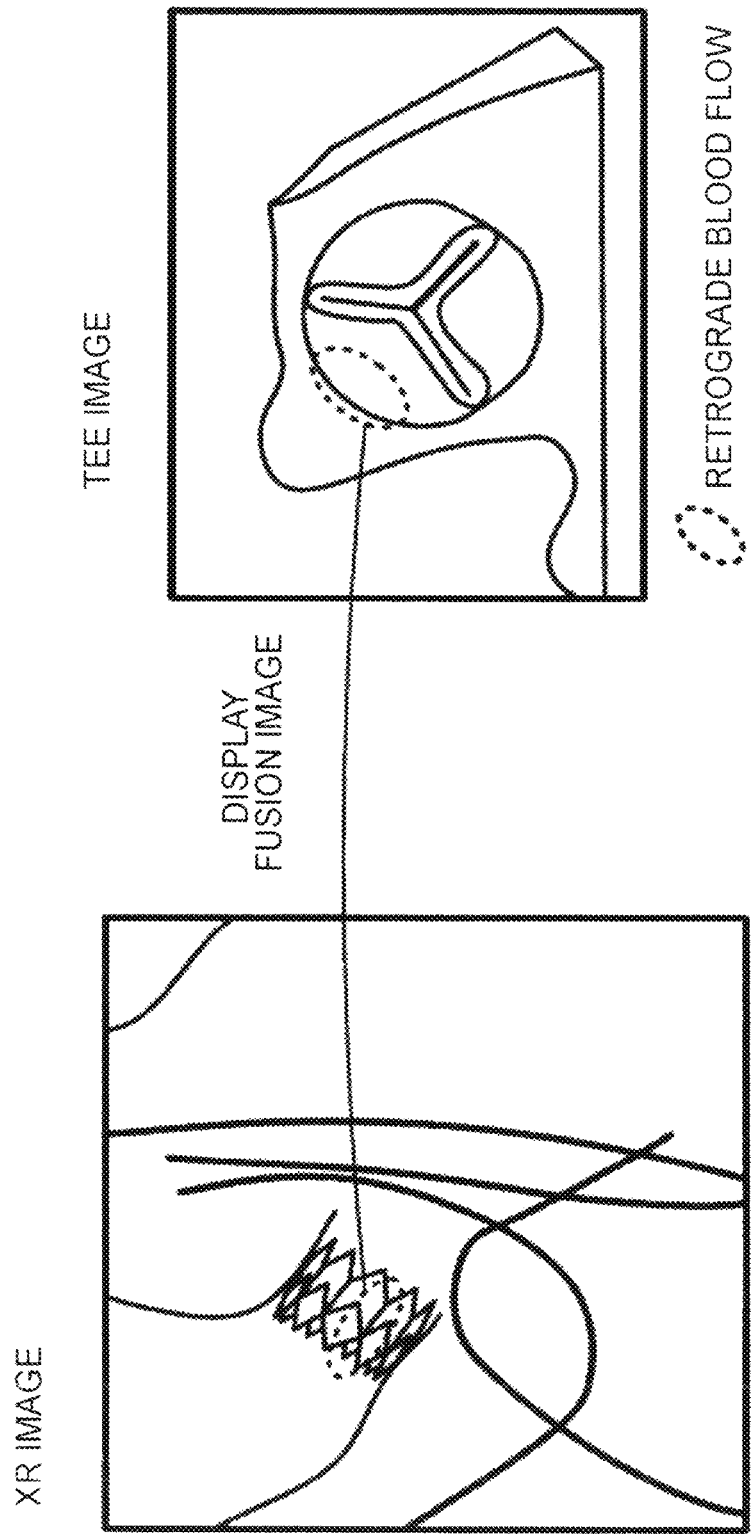
FIG. 5 is a diagram illustrating a display example of a fusion image in the first embodiment.

The display controller 14 displays the angiographic image and the reverse flow component (transesophageal ultrasound image), which has been registered to the angiographic image, together in a single display area ("fusion image display" in FIG. 2). FIG. 5 is a diagram illustrating a display example of a fusion image. FIG. 5 illustrates an XR image, in which a reverse flow component (transesophageal ultrasound image) is indicated by a broken line. As illustrated in FIG. 5, the reverse flow component (transesophageal ultrasound image) is located in a space of the angiography apparatus 2. As to the reverse flow component axis, its position and orientation are defined in the space. Thus, the displayed reverse flow component can be observed from the side. Father, since less overlap is created between the reverse flow component and the therapeutic valve, the reverse flow component can be easily observed.

<Modification>

A modification of the first embodiment is described with reference to FIG. 6. In the aortic region, the reverse flow component is present in a forward flow component (antegrade blood flow). For this reason, when the reverse flow component is located on the rear side of the forward flow component as viewed from the capturing direction of the angiography apparatus 2, it is difficult to observe the reverse flow component. Therefore, in the modification of the first embodiment, the capturing direction controller 13 controls the capturing direction of the angiography apparatus 2 (the optimum angle of the C-arm) such that less overlap is created between the reverse flow component and the therapeutic valve as well as that the forward flow component is located on the rear side or alongside of the reverse flow component. In other words, in this modification, the capturing direction controller 13 sets the capturing direction from the angle range of the C-arm so as to avoid the forward flow component, and also from the angle range in which the reverse flow component can be observed.

FIG. 6 illustrates the C-arm before and after the capturing direction is controlled. When a retrograde blood flow is located on the rear side of an antegrade blood flow as viewed from the capturing direction of the angiography apparatus 2 as illustrated on the left side of FIG. 6, the capturing direction controller 13 rotates the C-arm counterclockwise by a predetermined angle such that the retrograde blood flow and the antegrade blood flow are aligned side by side as illustrated on the right side of FIG. 6.

Second Embodiment

Figure 7:
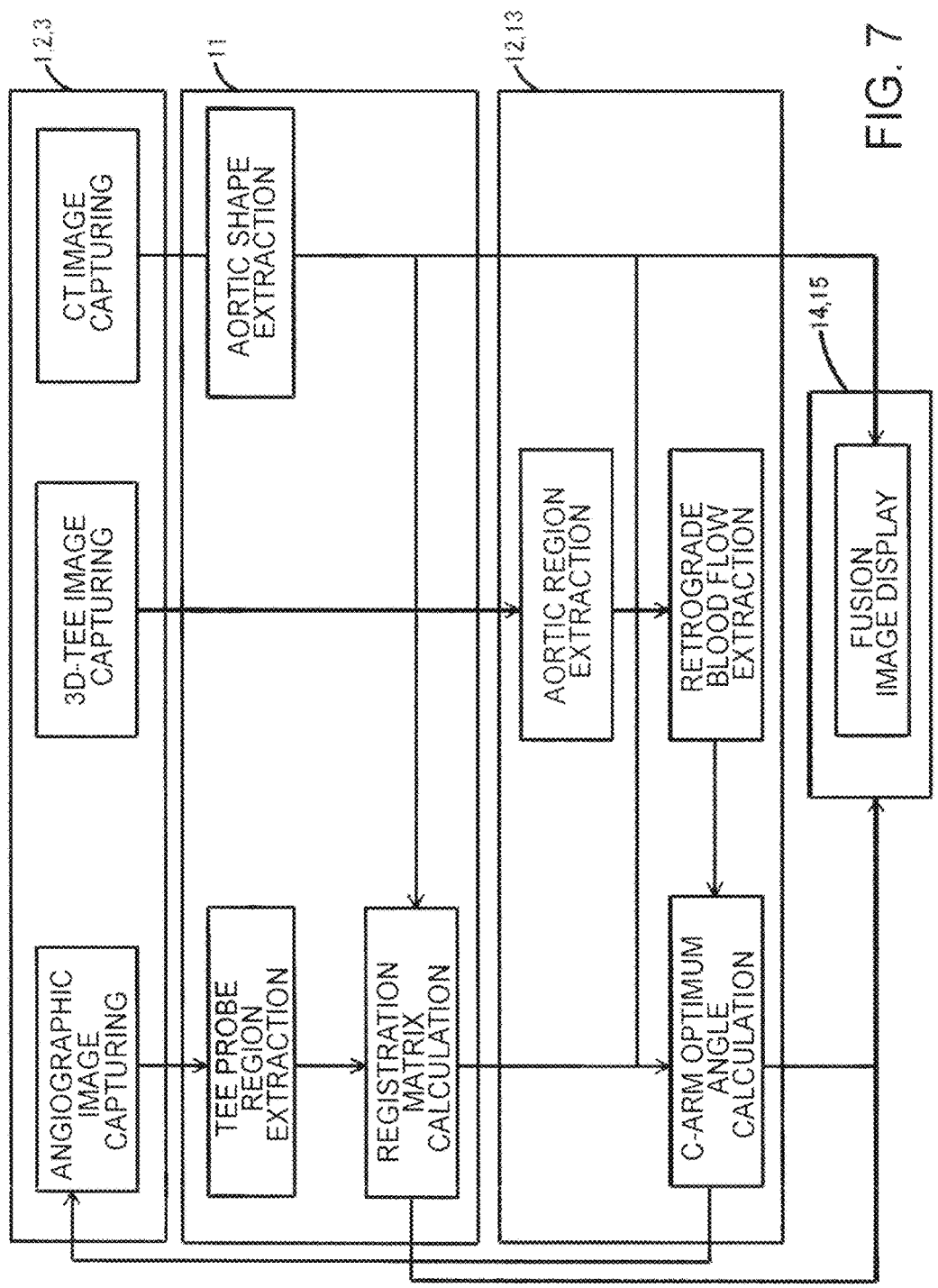
FIG. 7 is a block diagram of a medical system according to a second embodiment.
Figure 8:
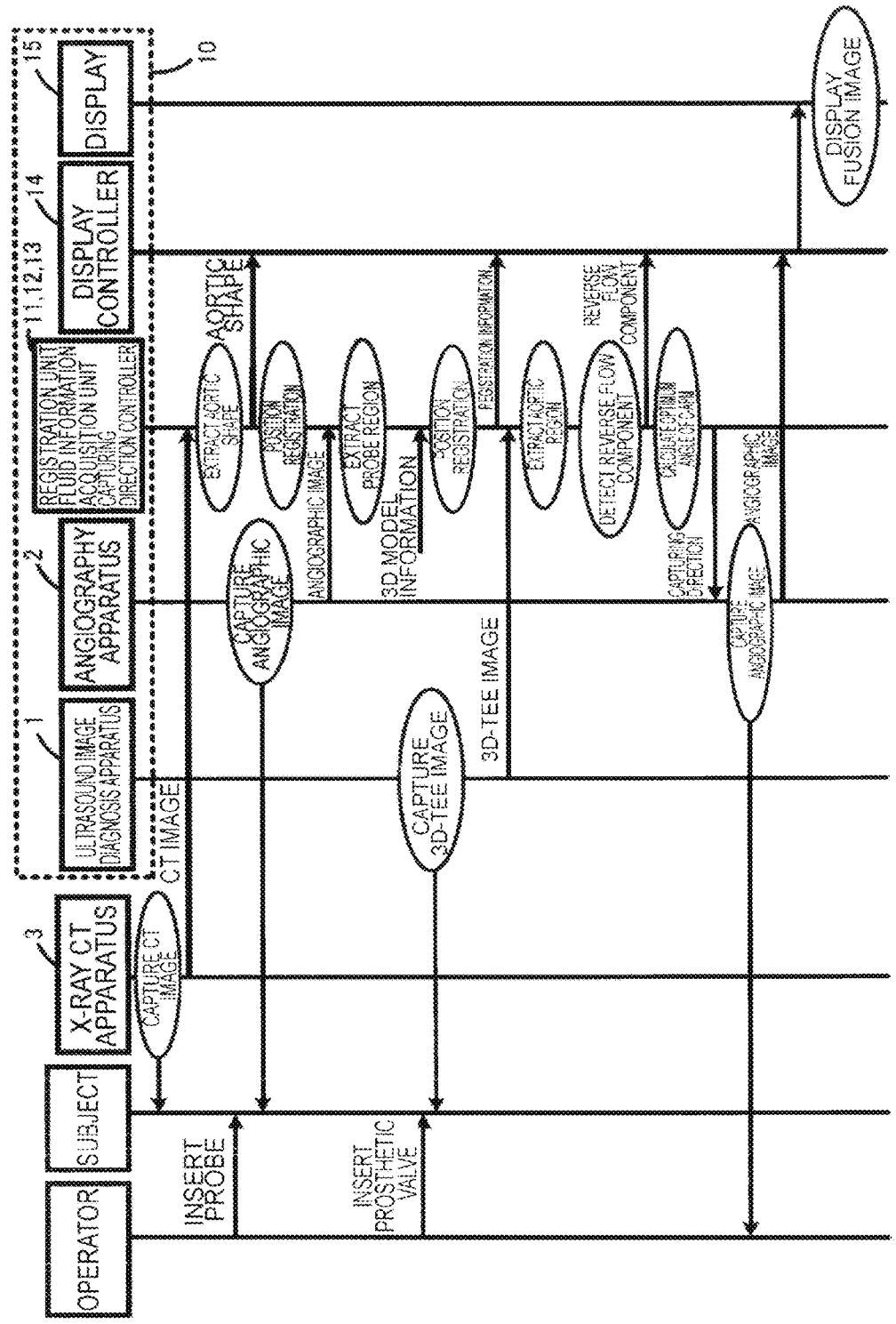
FIG. 8 is a timing chart illustrating the operation of the medical system of the second embodiment.
Figure 9:
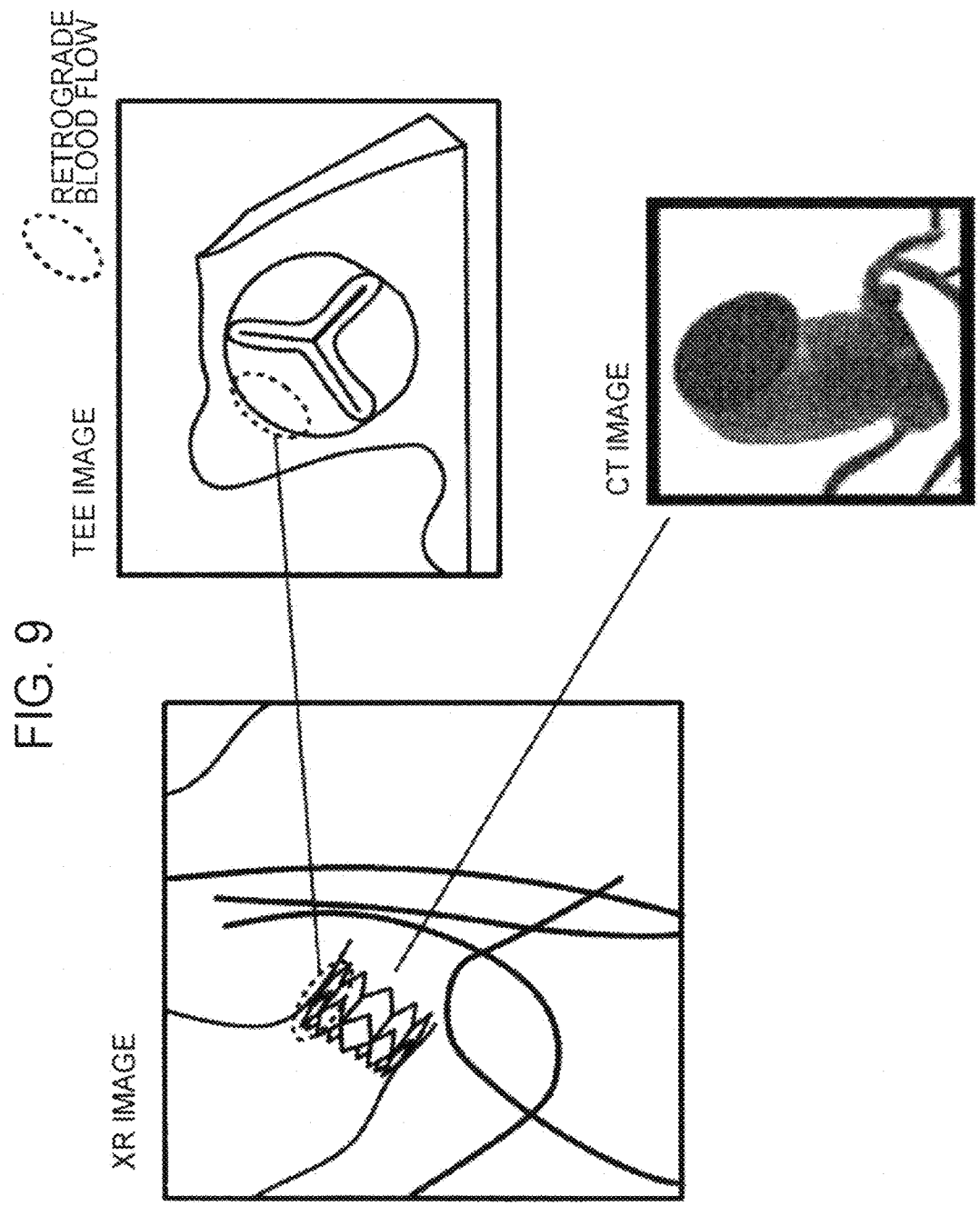
FIG. 9 is a diagram illustrating a display example of a fusion image in the second embodiment.

Next, the second embodiment is described with reference to FIGS. 7 to 9. FIG. 7 is a block diagram of a medical system according to the second embodiment. FIG. 8 is a timing chart illustrating the operation of the medical system. In the following, the same description as already given in the first embodiment is not repeated, and differences are mainly described.

In the first embodiment and the modification thereof, the capturing direction controller 13 controls the capturing direction of the angiography apparatus 2 based on the reverse flow component that includes the reverse flow component axis, and the location of the therapeutic valve and the forward flow component.

In the second embodiment, the capturing direction controller 13 controls the capturing direction based further on the valve structure. The term "valve structure" as used herein refers to the structure of the tricuspid aortic valves, the origins of the left and right coronary arteries, and other anatomical sites or their surroundings.

This embodiment is described taking the tricuspid aortic valves and the origins of the left and right coronary arteries as an example.

The shape of the valve structure before treatment is useful upon making a treatment plan previous to TAVR. A morphological image such as a CT image is used to recognize the structure of the tricuspid aortic valves and the origins of the left and right coronary arteries. Therefore, before TAVR, for example, the valve structure is captured by an X-ray CT apparatus 3 to capture a CT image ("CT image capturing" in FIGS. 7 and 8).

Before or during TAVR, the registration unit 11 extracts the tricuspid aortic valves and the origins of the left and right coronary arteries from the CT image ("aortic shape extraction" in FIGS. 7 and 8). Further, as in the aforementioned case of the transesophageal ultrasound image, the registration unit 11 registers the valve structure (the tricuspid aortic valves and/or the origins of the left and right coronary arteries) with respect to the angiography image.

In TAVR, in response to the selection of the reverse flow component, the therapeutic valve, and the valve structure (the tricuspid aortic valves and/or the origins of the left and right coronary arteries), the capturing direction controller 13 controls the capturing direction of the angiography apparatus 2 (the optimum angle of the C-arm) to reduce the overlap not only between the reverse flow component and the therapeutic valve but also between the tricuspid aortic valves and/or the origins of the left and right coronary arteries. Thereby, the capturing direction of the angiography apparatus 2 (angular position of the C-arm) can be determined to facilitate the observation from a viewpoint of the structure and the fluid. FIG. 9 illustrates a display example of a fusion image. FIG. 9 illustrates an XR image, in which a reverse flow component (transesophageal ultrasound image) is indicated by a broken line. As illustrated in FIG. 9, the reverse flow component (transesophageal ultrasound image) and the valve structure extracted from the CT image (the tricuspid aortic valves and/or the origins of the left and right coronary arteries) are located in a space of the angiography apparatus 2.

Third Embodiment

Figure 10:
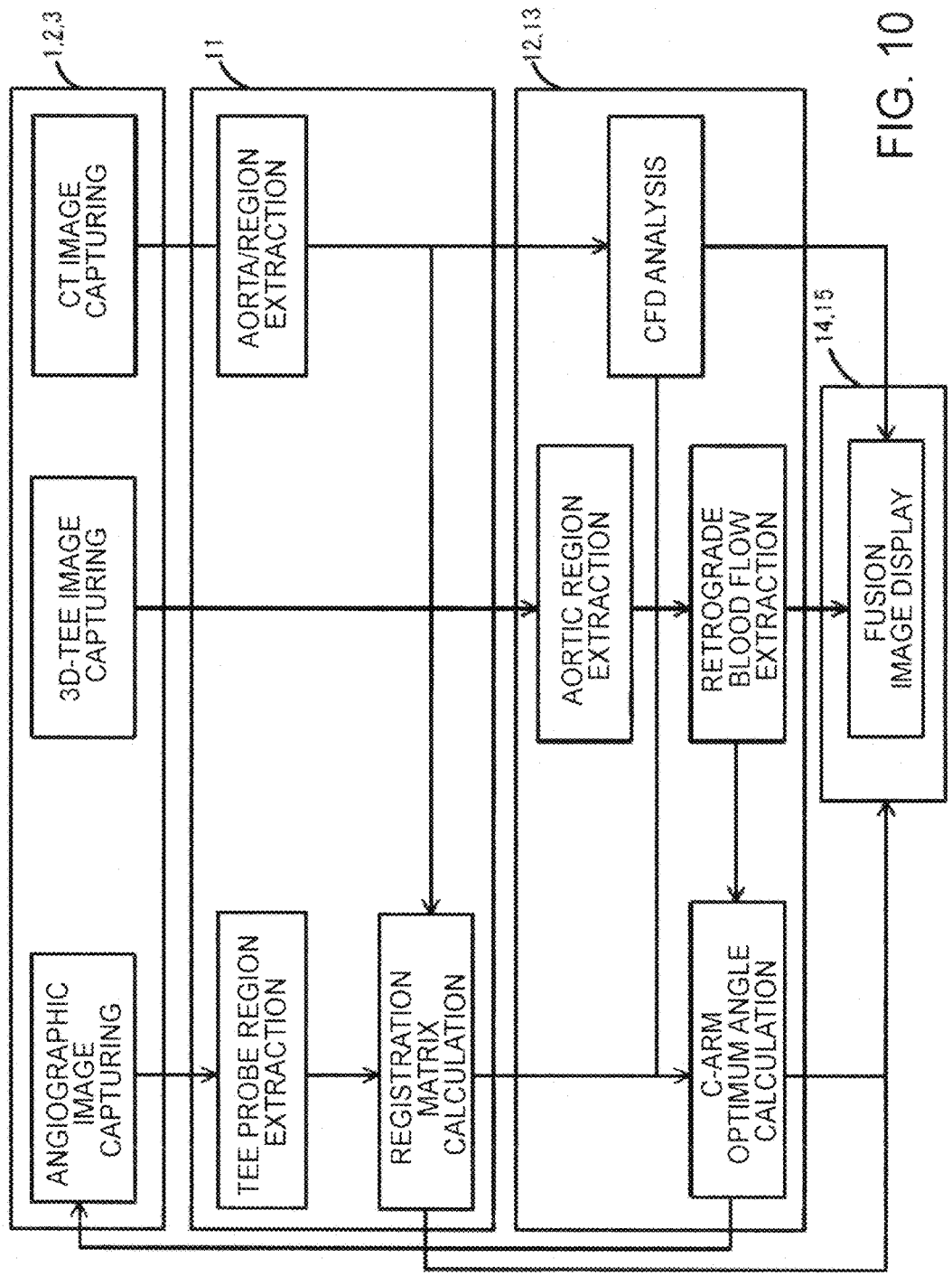
FIG. 10 is a block diagram of a medical system according to a third embodiment.
Figure 11:
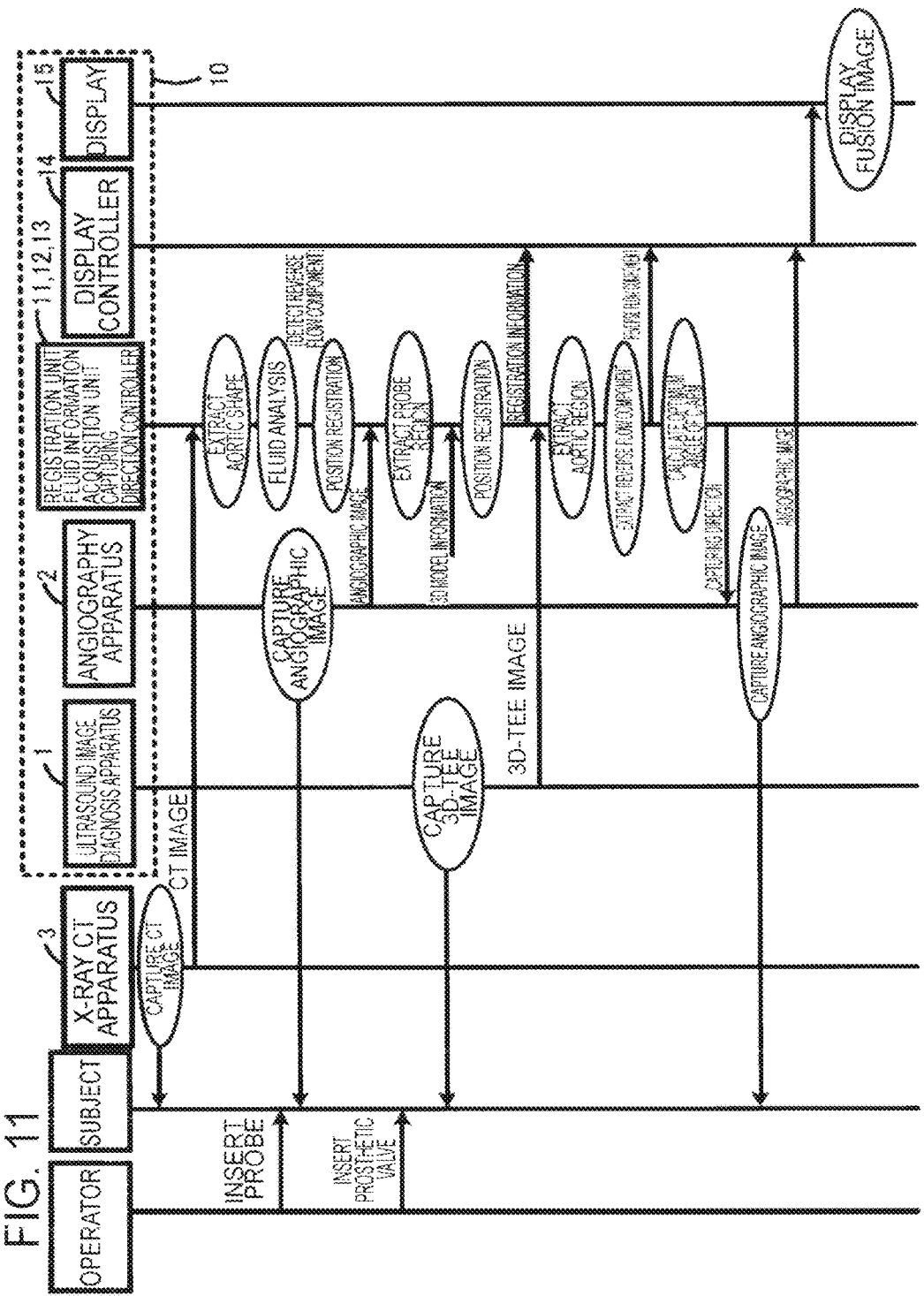
FIG. 11 is a timing chart illustrating the operation of the medical system of the third embodiment.

Next, the third embodiment is described with reference to FIGS. 10 to 12. FIG. 10 is a block diagram of a medical system according to the third embodiment. FIG. 11 is a timing chart illustrating the operation of the medical system. In the following, the same description as already given in the first embodiment is not repeated, and differences are mainly described.

In the first embodiment and the second embodiment, the fluid information acquisition unit 12 extracts a reverse flow component from a transesophageal ultrasound (3D-TEE) image, and the capturing direction controller 13 controls the capturing direction of the angiography apparatus 2 based on the reverse flow component extracted.

In the third embodiment, before TAVR, for example, the X-ray CT apparatus 3 captures a region of interest to thereby capture a CT image ("CT image capturing" in FIGS. 10 and 11). Further, the fluid information acquisition unit 12 performs a computational fluid dynamics (CFD) analysis on the CT image to acquire a reverse flow component for recognizing local blood flow vectors in the aorta ("CFD analysis" in FIG. 10, "fluid analysis" in FIG. 11). In addition, the registration unit 11 registers the reverse flow component with respect to the angiography image. During TAVR, the capturing direction controller 13 controls the capturing direction of the angiography apparatus 2 based on the reverse flow component thus acquired. A variety of known methods are available for the fluid analysis with a CT image. For example, the analysis may be performed using CFD according to an algorithm such as the finite volume method or the finite element method for analyzing a fluid (blood flow).

Figure 12:
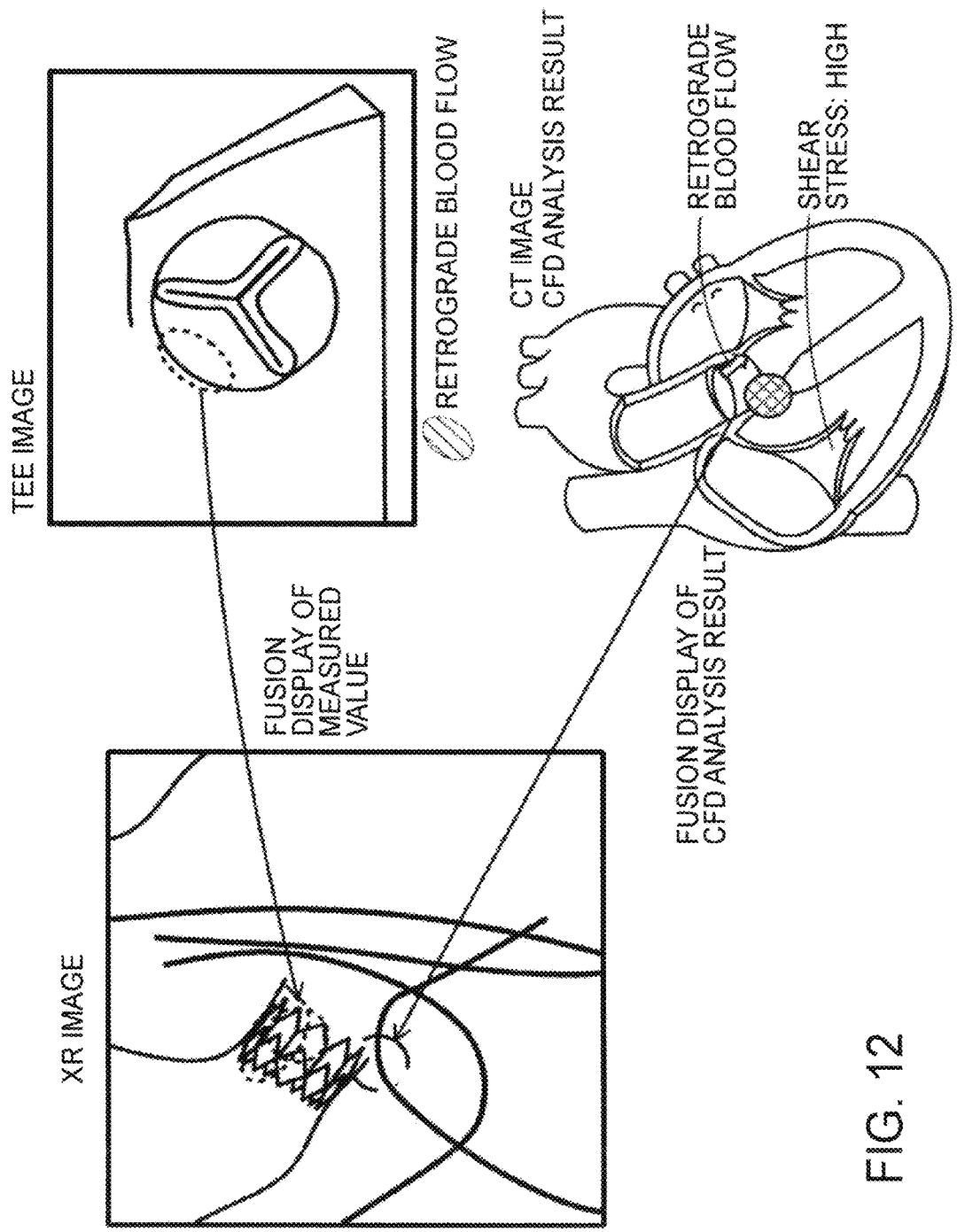
FIG. 12 is a diagram illustrating a display example of a fusion image in the third embodiment.

FIG. 12 illustrates a display example of a fusion image. FIG. 12 illustrates an XR image, in which a reverse flow component (transesophageal ultrasound image) is indicated by a broken line, and the analysis result is indicated by a chain line. As illustrated in FIG. 12, the reverse flow component (transesophageal ultrasound image) in the CT image and the analysis result are located in a space of the angiography apparatus 2. As a modification, blood flow conditions after treatment can be estimated through a reverse flow simulation performed after a prosthetic valve model has been added using CFD technique.

Fourth Embodiment

Figure 13:
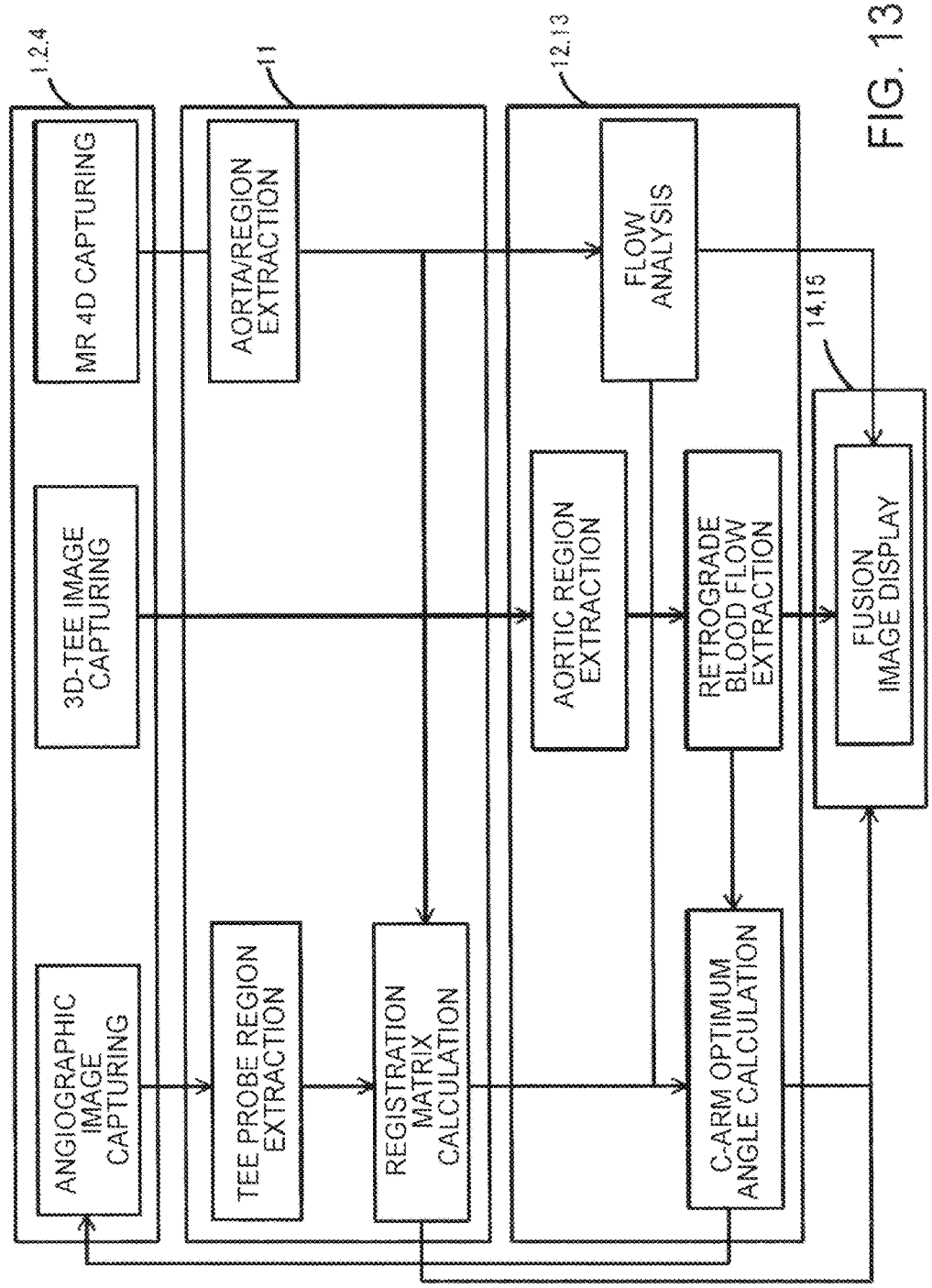
FIG. 13 is a block diagram of a medical system according to a fourth embodiment.
Figure 14:
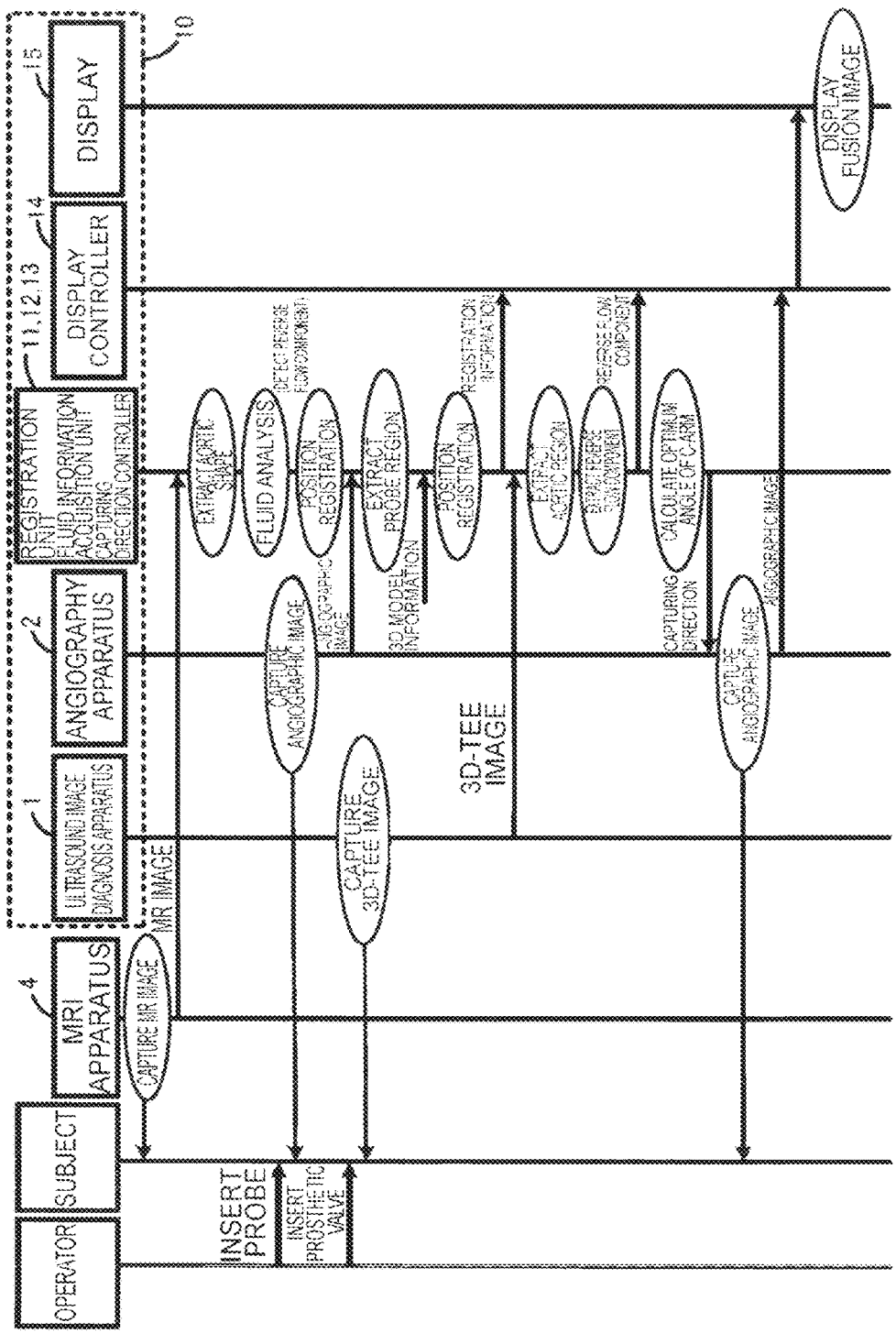
FIG. 14 is a timing chart illustrating the operation of the medical system of the fourth embodiment.

Next, a fourth embodiment is described with reference to FIGS. 13 to 15. FIG. 13 is a block diagram of a medical system according to the fourth embodiment. FIG. 14 is a timing chart illustrating the operation of the medical system. In the following, the same description as already given in the first embodiment is not repeated, and differences are mainly described.

In the fourth embodiment, as in the third embodiment, before TAVR, for example, a region of interest is captured by an MRI apparatus 4 to capture an MR image ("MR 4D capturing" in FIGS. 13 and 14). Further, the fluid information acquisition unit 12 performs a fluid analysis (flow analysis) on the MR image to extract a blood flow component in the aorta, and acquire a reverse flow component from the blood flow component ("flow analysis" in FIG. 13, "fluid analysis" in FIG. 14). In addition, the registration unit 11 registers the reverse flow component with respect to the angiography image. During TAVR, the capturing direction controller 13 controls the capturing direction of the angiography apparatus 2 based on the reverse flow component thus acquired. A variety of known methods are available for the flow analysis with an MR image. For example, JP-A No. 2011-131041 discloses a technology for obtaining information that represents the dynamics of a fluid based on a non-contrast-enhanced fluid MR image or a contrast-enhanced fluid MR image collected by the MRI apparatus 4.

Figure 15:
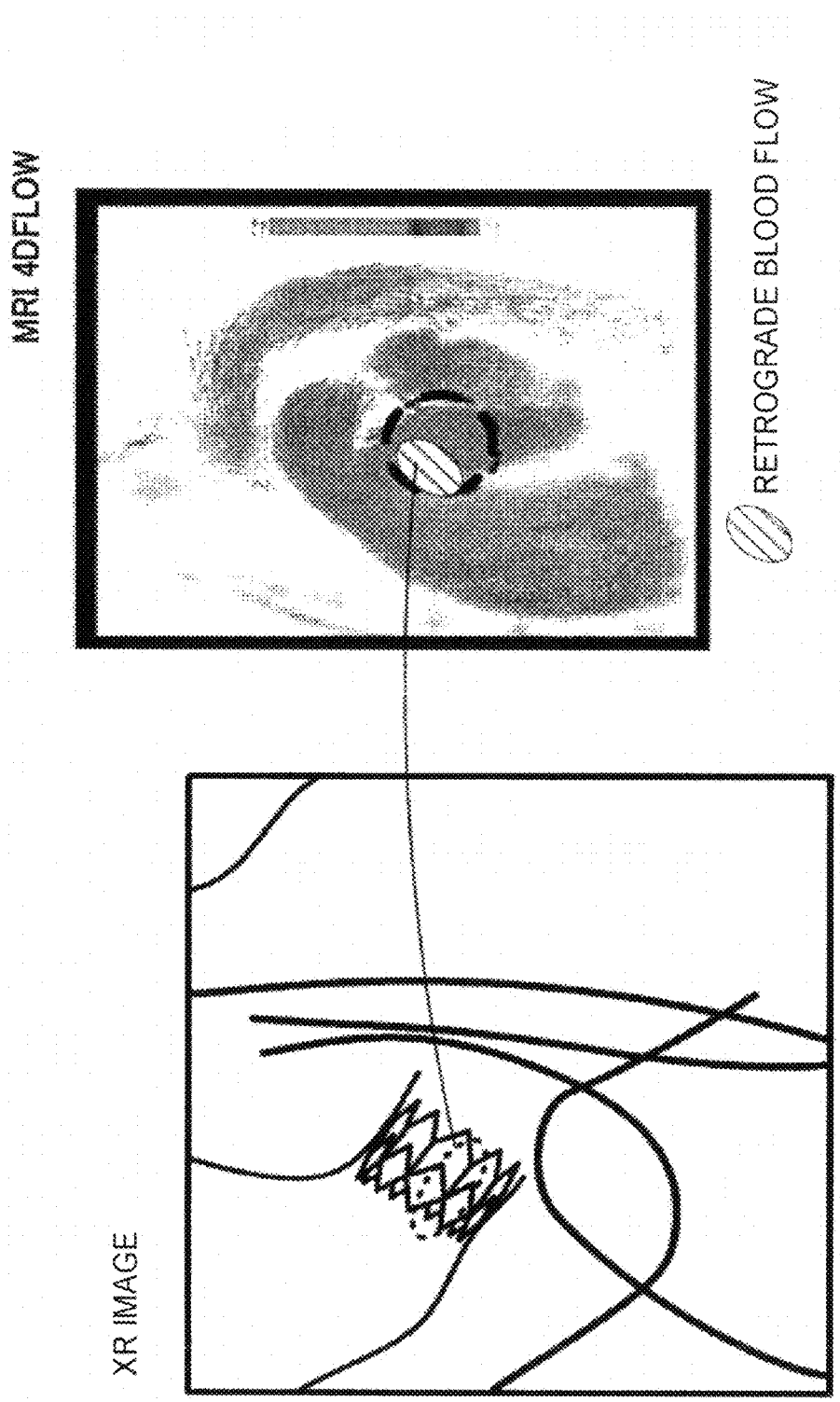
FIG. 15 is a diagram illustrating a display example of a fusion image in the fourth embodiment.

FIG. 15 illustrates a display example of a fusion image. FIG. 15 illustrates an XR image, in which a reverse flow component (transesophageal ultrasound image) is indicated by a broken line. As illustrated in FIG. 15, the reverse flow component (transesophageal ultrasound image) in the MR image is located in a space of the angiography apparatus 2.

In the above embodiments, an example is described in which the position and orientation of the probe are detected. For another example, a position detection system may be employed to detect the probe. The position detection system includes a magnetic transmitter arranged on the bed, and a magnetic sensor arranged on the probe. In this system, for example, the magnetic field of the magnetic transmitter is applied in X, Y, and Z directions, which are switched at a constant frequency. The magnetic sensor detects the position of X, Y, and Z and rotation about each axes, thereby detecting the position and orientation of the XYZ coordinates of the probe.

In the above embodiments, an example is described in which the capturing direction controller 13 controls the capturing direction of the angiography apparatus 2 based on a reverse flow component. However, it is not a limitation. Obviously, the capturing direction controller 13 may control the capturing direction of the angiography apparatus 2 based on a forward flow component.

The embodiments may be applied to, for example, an X-ray image diagnosis apparatus and a medical system for use in the replacement of heart valves other than the aortic valves, potential therapy for the myocardium (ablation, pacemakers, etc.), and the catheterization of large vessels other than the aorta. In this case, depending on the therapeutic purpose, a medical practitioner may set information on blood flow stoppage and blood flow leakage from the balloon as fluid Information as appropriate.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray image diagnosis apparatus, comprising:
an X-ray tube configured to emit X-rays toward a subject;
an X-ray detector configured to detect the X-rays having passed through the subject; and
processing circuitry configured to
acquire fluid information on a target site including a region of interest of the subject captured by an ultrasound image diagnosis apparatus,
extract position information of a probe of the ultrasound image diagnosis apparatus, and
control a capturing direction for capturing the target site based on the position information and a direction in which a fluid flows, which is indicated by the fluid information, wherein
the fluid information includes information on a forward flow component as a normal blood flow and a reverse flow component as an abnormal blood flow in a prosthetic valve placed in the region of interest, and
the processing circuitry is further configured to obtain the capturing direction with the X-rays based on a position of the reverse flow component.

2. The X-ray image diagnosis apparatus of claim 1, wherein the processing circuitry is further configured to acquire a Doppler image as the fluid information based on ultrasound waves exchanged between the probe and the subject.

3. The X-ray image diagnosis apparatus of claim 2, wherein the processing circuitry is further configured to
acquire a plurality of Doppler images in time series to extract the reverse flow component therefrom,
specify an image of a time phase, in which the reverse flow component has a largest volume, from the Doppler images, and
obtain a direction of the reverse flow component, which serves as a reference to control the capturing direction with the X-rays, with respect to the volume in the image specified.

4. The X-ray image diagnosis apparatus of claim 1, wherein the processing circuitry is further configured to control the capturing direction to have less overlap between the reverse flow component and the prosthetic valve as viewed from the capturing direction with the X-rays.

5. The X-ray image diagnosis apparatus of claim 4, wherein the processing circuitry is further configured to control the capturing direction such that, in the region of interest, the forward flow component is located on a rear side or alongside of the reverse flow component as viewed from the capturing direction.

6. The X-ray image diagnosis apparatus of claim 4, wherein the processing circuitry is further configured to control the capturing direction to have less overlap between tricuspid aortic valves and/or origins of coronary arteries in addition to between the reverse flow component and the prosthetic valve.

7. A medical system, comprising:
an X-ray image diagnosis apparatus including an X-ray tube configured to emit X-rays toward a subject, and an X-ray detector configured to detect the X-rays having passed through the subject; and
an ultrasound image diagnosis apparatus configured to capture a target site including a region of interest of the subject,
wherein the X-ray image diagnosis apparatus further includes processing circuitry configured to
acquire fluid information on the target site,
extract position information of a probe of the ultrasound image diagnosis apparatus, and
control a capturing direction for capturing the target site based on the position information and a direction in which a fluid flows indicated by the fluid information wherein
the ultrasound image diagnosis apparatus and the X-ray image diagnosis apparatus are configured to perform capturing of the target site in order, wherein the ultrasound image diagnosis apparatus is further configured to perform the capturing by the probe in the subject, and
images captured by the apparatuses are displayed to enable observation of blood flow conditions in the region of interest and a periphery thereof.

8. The medical system of claim 7, wherein the processing circuitry is further configured to
determine registration information for position registration between an image captured by the probe and an image captured by the X-ray image diagnosis apparatus with reference to a three-dimensional model representing a shape of the probe based on an image of the probe in the subject captured by the X-ray image diagnosis apparatus, and
display a combination of the image captured by the ultrasound image diagnosis apparatus and the image captured by the X-ray image diagnosis apparatus, the capturing direction of which has been controlled.

9. The medical system of claim 8, further comprising at least one of an X-ray CT apparatus and an MRI apparatus,
wherein the ultrasound image diagnosis apparatus and the X-ray image diagnosis apparatus are configured to perform capturing of the target site in order, wherein the ultrasound image diagnosis apparatus is configured to perform the capturing by the probe in the subject,
images captured by the apparatuses are displayed to enable observation of blood flow conditions in the region of interest and a periphery thereof, and
the processing circuitry is further configured to
acquire the fluid information in the region of interest based on an image of the target site captured by either or both of the X-ray CT apparatus and the MRI apparatus, and
control the capturing direction of the X-ray image diagnosis apparatus based on the direction in which the fluid flows, which is indicated by the fluid information acquired.

10. The medical system of claim 9, wherein the processing circuitry is further configured to analyze either or both of a CT image and an MR image as the image of the target site to obtain the direction in which the fluid flows, which is indicated by the fluid information.

* * * * *